United States Patent
El-Sherbeini et al.

(10) Patent No.: US 7,022,829 B1
(45) Date of Patent: Apr. 4, 2006

(54) **MURC GENE AND ENZYME OF *PSEUDOMONAS AERUGINOSA***

(75) Inventors: Mohamend El-Sherbeini, Westfield, NJ (US); Barbara Azzolina, Denville, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/070,780

(22) PCT Filed: Sep. 11, 2000

(86) PCT No.: PCT/US00/24845

§ 371 (c)(1),
(2), (4) Date: Mar. 7, 2002

(87) PCT Pub. No.: WO01/19979

PCT Pub. Date: Mar. 22, 2001

Related U.S. Application Data (60) Provisional application No. 60/154,073, filed on Sep. 14, 1999.

(51) Int. Cl.
*A61K 31/70* (2006.01)

(52) U.S. Cl. .................. 536/23.7; 435/4; 435/69.1; 435/252.3; 435/71.1; 530/350; 530/300; 514/44

(58) Field of Classification Search .................. 514/44; 536/23.1, 24.32, 23.3, 23.5, 23.7, 24.3, 23.6; 530/350; 424/234.1, 184.1, 1.11; 435/7.2, 435/18, 183, 15, 19, 24, 243, 4, 32, 471, 435/6, 69.1, 69.8, 7.1, 7.32, 7.4, 252.33, 435/320.1, 325, 362, 365, 367, 16, 21, 23, 435/7.91, 320, 440, 71.1, 71.2
See application file for complete search history.

(56) References Cited

U.S. PATENT DOCUMENTS

| | | | |
|---|---|---|---|
| 5,891,621 A * | 4/1999 | Chabin et al. .................. 435/4 |
| 6,211,161 B1 * | 4/2001 | Beattie et al. ................ 514/44 |
| 6,310,193 B1 * | 10/2001 | Black et al. ................ 536/23.5 |
| 6,838,255 B1 * | 1/2005 | Burnham .................... 435/69.1 |
| 6,870,041 B1 * | 3/2005 | El-Sherbeini et al. ...... 536/23.7 |
| 6,890,910 B1 * | 5/2005 | El-Sherbeini et al. ......... 514/44 |
| 6,949,336 B1 * | 9/2005 | El-Sherbeini et al. .......... 435/4 |
| 2002/0015678 A1 * | 2/2002 | Yuan et al. ................. 424/1.11 |
| 2004/0052799 A1 * | 3/2004 | Smith et al. ............. 424/184.1 |

* cited by examiner

*Primary Examiner*—Lynette R. F. Smith
*Assistant Examiner*—Ginny Allen Portner
(74) *Attorney, Agent, or Firm*—Michael D. Yablonsky; Jack L. Tribble (57) ABSTRACT

This invention provides isolated polynucleotides that encode the MurC protein of *Pseudomonas aeruginosa*. Purified and isolated MurC recombinant proteins are also provided. Nucleic acid sequences which encode functionally active MurC proteins are described. Assays for the identification of modulators of the of expression of murC and inhibitors of the activity of MurC, are also provided.

11 Claims, 3 Drawing Sheets

FIG 1A

```
  1   ctccatggcagaccaggcacgcagcctggcgaaacccgaggctacccggacggtggtcga    60
      gaggtaccgtctggtccgtgcgtcggaccgctttgggctccgatgggcctgccaccagct
                                                                 Met 61   tgcctgcctggaggtggcccgtggttaaagaaccgaatggcgtcacccggaccatgcgcc   120
      acggacggacctccaccgggcaccaatttcttggcttaccgcagtgggcctggtacgcgg
         ProAlaTrpArgTrpProValValLysGluProAsnGlyValThrArgThrMetArgArg 121   gtatccgccgcatccatttcgtcggcatcggcggcgccggtatgtgcgggatcgccgaag   180
      cataggcggcgtaggtaaagcagccgtagccgccgcggccatacacgccctagcggcttc
         IleArgArgIleHisPheValGlyIleGlyGlyAlaGlyMetCysGlyIleAlaGluVal 181   tgctgctgaacctcggctacgaggtatccggctcggacctcaaggcctcggcggtgaccg   240
      acgacgacttggagccgatgctccataggccgagcctggagttccggagccgccactggc
         LeuLeuAsnLeuGlyTyrGluValSerGlySerAspLeuLysAlaSerAlaValThrGlu 241   agcgcctggagaagttcggcgcgcagatcttcatcggccaccaggcggaaaacgccgacg   300
      tcgcggacctcttcaagccgcgcgtctagaagtagccggtggtccgccttttgcggctgc
         ArgLeuGluLysPheGlyAlaGlnIlePheIleGlyHisGlnAlaGluAsnAlaAspGly 301   gcgccgacgtgctggtggtgtccagtgccatcaaccgggccaacccggaagtggcatcgg   360
      cgcggctgcacgaccaccacaggtcacggtagttggcccggttgggccttcaccgtagcc
         AlaAspValLeuValValSerSerAlaIleAsnArgAlaAsnProGluValAlaSerAla 361   ccctggaacggcggattccggtggtgccgcgtgcggagatgctcgccgagctgatgcgct   420
      gggaccttgccgcctaaggccaccacggcgcacgcctctacgagcggctcgactacgcga
         LeuGluArgArgIleProValValProArgAlaGluMetLeuAlaGluLeuMetArgTyr 421   accggcacggcatcgcggtagccggcacccacggcaagaccaccactaccagcctgatcg   480
      tggccgtgccgtagcgccatcggccgtgggtgccgttctggtggtgatggtcggactagc
         ArgHisGlyIleAlaValAlaGlyThrHisGlyLysThrThrThrThrSerLeuIleAla 481   cctcggtgttcgccgccggcggcctggacccgaccttcgtcatcggcggccggctgaacg   540
      ggagccacaagcggcggccgccggacctgggctggaagcagtagccgccggccgacttgc
         SerValPheAlaAlaGlyGlyLeuAspProThrPheValIleGlyGlyArgLeuAsnAla 541   ccgccgggaccaacgcccagctcggcgccagccgctacctggtggccgaggccgacgaga   600
      ggcggccctggttgcgggtcgagccgcggtcggcgatggaccaccggctccggctgctct
         AlaGlyThrAsnAlaGlnLeuGlyAlaSerArgTyrLeuValAlaGluAlaAspGluSer 601   gcgacgccagcttcctgcacctgcaaccgatggtcgcggtggtcaccaatatcgacgccg   660
      cgctgcggtcgaaggacgtggacgttggctaccagcgccaccagtggttatagctgcggc
         AspAlaSerPheLeuHisLeuGlnProMetValAlaValValThrAsnIleAspAlaAsp 661   accacatggcgacctacggcggcgacttcaacaagctgaagaagaccttcgtcgagttcc   720
      tggtgtaccgctggatgccgccgctgaagttgttcgacttcttctggaagcagctcaagg
         HisMetAlaThrTyrGlyGlyAspPheAsnLysLeuLysLysThrPheValGluPheLeu 721   tccacaacctgccgttctacggactggcggtgatgtgcgtggatgatccggttgtgcgtg   780
      aggtgttggacggcaagatgcctgaccgccactacacgcacctactaggccaacacgcac
         HisAsnLeuProPheTyrGlyLeuAlaValMetCysValAspAspProValValArgGlu
```

FIG 1B

```
 781   agatcctcccgcagatcgcccgcccgaccgtgacctacggcctcagcgaagacgccgacg    840
       tctaggagggcgtctagcgggcgggctggcactggatgccggagtcgcttctgcggctgc
          IleLeuProGlnIleAlaArgProThrValThrTyrGlyLeuSerGluAspAlaAspVal 841   tgcgcgcgatcaacatccgccaggaaggcatgcgcacctggttcaccgtgttgcgcccgg    900
       acgcgcgctagttgtaggcggtccttccgtacgcgtggaccaagtggcacaacgcgggcc
          ArgAlaIleAsnIleArgGlnGluGlyMetArgThrTrpPheThrValLeuArgProGlu 901   agcgcgagccgctggacgtctcggtgaacatgcccggcctgcacaacgtgctgaattccc    960
       tcgcgctcggcgacctgcagagccacttgtacgggccggacgtgttgcacgacttaaggg
          ArgGluProLeuAspValSerValAsnMetProGlyLeuHisAsnValLeuAsnSerLeu 961   tggcgaccatcgtcatcgctaccgacgagggcatctccgacgaagccatcgtccagggc    1020
       accgctggtagcagtagcgatggctgctcccgtagaggctgcttcggtagcaggtccccg
          AlaThrIleValIleAlaThrAspGluGlyIleSerAspGluAlaIleValGlnGlyLeu 1021   tgtccggcttccagggcgtaggccggcgcttccaggtctacggcgagctgcaggtcgagg    1080
       acaggccgaaggtcccgcatccggccgcgaaggtccagatgccgctcgacgtccagctcc
          SerGlyPheGlnGlyValGlyArgArgPheGlnValTyrGlyGluLeuGlnValGluGly 1081   gtggcagcgtgatgctggtggacgattacggccaccatccgcgcgaagtcgccgcggtga    1140
       caccgtcgcactacgaccacctgctaatgccggtggtaggcgcgcttcagcggcgccact
          GlySerValMetLeuValAspAspTyrGlyHisHisProArgGluValAlaAlaValIle 1141   tcaaggcgatccgtggcggttggccggagcgtcgcctggtgatggtctaccagccgcatc    1200
       agttccgctaggcaccgccaaccggcctcgcagcggaccactaccagatggtcggcgtag
          LysAlaIleArgGlyGlyTrpProGluArgArgLeuValMetValTyrGlnProHisArg 1201   gctatacccgtacccgcgacctgtacgaagacttcgtgcaggtgctgggcgaagccaacg    1260
       cgatatgggcatgggcgctggacatgcttctgaagcacgtccacgacccgcttcggttgc
          TyrThrArgThrArgAspLeuTyrGluAspPheValGlnValLeuGlyGluAlaAsnVal 1261   tgctgctgttgatggaggtctatccggccggcgaagagccgatcccgggagccgacagcc    1320
       acgacgacaactacctccagataggccggccgcttctcggctagggccctcggctgtcgg
          LeuLeuLeuMetGluValTyrProAlaGlyGluGluProIleProGlyAlaAspSerArg

1321   gccagctgtgccacagcatccgccagcgcggccagcttgacccgatctacttcgagcgcg    1380
       cggtcgacacggtgtcgtaggcggtcgcgccggtcgaactgggctagatgaagctcgcgc
          GlnLeuCysHisSerIleArgGlnArgGlyGlnLeuAspProIleTyrPheGluArgAsp 1381   acgccgacctggcgccgctggtcaagccgctgctgcgcgctggcgacatcctgctttgcc    1440
       tgcggctggaccgcggcgaccagttcggcgacgacgcgcgaccgctgtaggacgaaacgg
          AlaAspLeuAlaProLeuValLysProLeuLeuArgAlaGlyAspIleLeuLeuCysGln 1441   agggcgctggcgatgtcggcggcctggccccgcaactgatcaagaacccgctgttcgccg    1500
       tcccgcgaccgctacagccgccggaccggggcgttgactagttcttgggcgacaagcggc
          GlyAlaGlyAspValGlyGlyLeuAlaProGlnLeuIleLysAsnProLeuPheAlaGly 1501   gcaagggagggaagggcgcatgaacctttgcctcgatagcctgctgaacg             1550
       cgttccctcccttcccgcgtacttggaaacggagctatcggacgacttgc
          LysGlyGlyLysGlyAla
```

FIG. 2

MURC GENE AND ENZYME OF PSEUDOMONAS AERUGINOSA

CROSS-REFERENCE TO RELATED APPLICATIONS

This application claims the benefit of U.S. Provisional Application No. 60/154,073, filed Sep. 14, 1999, and is a National Stage Filing of PCT/US00/24845, having an International Filing Date of Sep. 11, 2000, the contents of which are incorporated herein by reference in their entirety.

FIELD OF THE INVENTION

This invention relates to the genes and enzymes involved in cell wall synthesis in bacteria, and particularly to the inhibition of such enzymes.

BACKGROUND OF THE INVENTION

The emegence of mluti-drug resistant bacteria has led to an increased demand for new antibiotics with new modes of action. The biosynthetic pathway of the bacterial cell wall contains several attractive targets. Some of the enzymes in that pathway are proven targets for antibiotics such as β-lactams and glycopeptides antibiotics.

The bacterial cell wall is a polymer—a single molecule composed of peptidoglycan—that defines the boundary and shape of the cell. Assembled by crosslinking glycan chains with short peptide bridges (Rogers, H. J., H. R. Perkins, and J. B. Ward, 1980, Biosynthesis of peptidoglycan. p. 239–297. In Microbial cell walls and membranes. Chapman & Hall Ltd. London), the completed structure is strong enough to maintain cell integrity against an osmotic pressure differential of over four atmospheres, but also flexible enough to allow the cell to move, grow and divide.

The construction of the peptidoglycan begins in the cytoplasm with an activated sugar molecule, UDP-N-acetyl-glucosamine. After two reactions (catalyzed by MurA and MurB) that result in the placement of a lactyl group on the 3-OH of the glucosamine moiety, a series of ATP-dependent amino acid ligases (MurC, -D, -E, and -F) catalyze the stepwise synthesis of the pentapeptide sidechain using the newly synthesized lactyl carboxylate as the first acceptor site. After attachment of the sugar pentapeptide to a lipid carrier in the plasma membrane, another glucosamine unit is added to the 4-OH of the muramic acid moiety. The completed monomeric building block is moved across the membrane into the periplasm where the penicillin-binding proteins enzymatically add it into the growing cell wall (Lugtenberg, E. J. J., 1972, Studies on *Escherichia coli* enzymes involved in the synthesis of Uridine Diphosphate-N-Acetyl-Muramyl-pentapeptide. J. Bacteriol. 110:26–34; Mengin-Lecreulx, D., B. Flouret, and J. van Heijenoort, 1982, Cytoplasmic steps of peptidoglycan synthesis in *Escherichia coli*. J. Bacteriol. 151: 1109–1117).

Among the potential enzyme targets involved in cell wall biosynthesis is MurC, UDP-N-acetylmuramoyl ligase. This enzyme catalyses the ATP-dependent addition of L-alanine to UDP-N-acetylmuramoyl to form the precursor UDP-N-acetylmuramoyl-L-alanine. This step is essential for cell wall formation in both Gram (−ve) and Gram (+ve) bacteria. Thus, inhibitors of this enzyme are likely broad spectrum antibiotics.

SUMMARY OF THE INVENTION

Polynucleotides and polypeptides of *Pseudomonas aeruginosa* MurC, an enzyme involved in bacterial cell wall biosynthesis are provided. The recombinant MurC enzyme is catalytically active in ATP-dependent D-glutamate addition reactions. The enzyme is used in in vitro assays to screen for antibacterial compounds that target cell wall biosynthesis. The invention includes the polynucleotides, proteins encoded by the polynucleotides, and host cells expressing the recombinant enzyme, probes and primers, and the use of these molecules in assays.

An aspect of this invention is a polynucleotide having a sequence encoding a *Pseudomonas aeruginosa* MurC protein, or a complementary sequence. In a particular embodiment the encoded protein has a sequence corresponding to SEQ ID NO:2. In other embodiments, the encoded protein can be a naturally occurring mutant or polymorphic form of the protein. In preferred embodiments the polynucleotide can be DNA, RNA or a mixture of both, and can be single or double stranded. In particular embodiments, the polynucelotide is comprised of natural, non-natural or modified nucleotides. In some embodiments, the internucleotide linkages are linkages that occur in nature. In other embodiments, the internucleotide linkages can be non-natural linkages or a mixture of natural and non-natural linkages. In a most preferred embodiment, the polynucleotide has a sequence shown in SEQ ID NO:1.

An aspect of this invention is a polynucleotide having a sequence of at least about 25 contiguous nucleotides that is specific for a naturally occurring polynucleotide encoding a *Pseudomonas aeruginosa* MurC protein. In particular preferred embodiments, the polynucleotides of this aspect are useful as probes for the specific detection of the presence of a polynucleotide encoding a *Pseudomonas aeruginosa* MurC protein. In other particular embodiments, the polynucleotides of this aspect are useful as primers for use in nucleic acid amplification based assays for the specific detection of the presence of a polynucleotide encoding a *Pseudomonas aeruginosa* MurC protein. In preferred embodiments, the polynucleotides of this aspect can have additional components including, but not limited to, compounds, isotopes, proteins or sequences for the detection of the probe or primer.

An aspect of this invention is an expression vector including a polynucleotide encoding a *Pseudomonas aeruginosa* MurC protein, or a complementary sequence, and regulatory regions. In a particular embodiment the encoded protein has a sequence corresponding to SEQ ID NO:2. In particular embodiments, the vector can have any of a variety of regulatory regions known and used in the art as appropriate for the types of host cells the vector can be used in. In a most preferred embodiment, the vector has regulatory regions appropriate for the expression of the encoded protein in gram-negative prokaryotic host cells. In other embodiments, the vector has regulatory regions appropriate for expression of the encoded protein in gram-positive host cells, yeasts, cyanobacteria or actinomycetes. In some preferred embodiments the regulatory regions provide for inducible expression while in other preferred embodiments the regulatory regions provide for constitutive expression. Finally, according to this aspect, the expression vector can be derived from a plasmid, phage, virus or a combination thereof.

An aspect of this invention is host cell comprising an expression vector including a polynucleotide encoding a *Pseudomonas aeruginosa* MurC protein, or a complementary sequence, and regulatory regions. In a particular embodiment the encoded protein has a sequence corresponding to SEQ ID NO:2. In preferred embodiments, the host cell is a yeast, gram-positive bacterium, cyanobacterium or actinomycete. In a most preferred embodiment, the host cell is a gram-negative bacterium.

An aspect of this invention is a process for expressing a MurC protein of *P. aeruginosa* in a host cell. In this aspect a host cell is transformed or transfected with an expression vector including a polynucleotide encoding a *Pseudomonas* aeruginosa MurC protein, or a complementary sequence. According to this aspect, the host cell is cultured under conditions conducive to the expression of the encoded MurC protein. In particular embodiments the expression is inducible or constitutive. In a particular embodiment the encoded protein has a sequence corresponding to SEQ ID NO:2.

An aspect of this invention is a purified polypeptide having an amino acid sequence of SEQ ID NO:2 or the sequence of a naturally occurring mutant or polymorphic form of the protein.

An aspect of this invention is a method of determining whether a candidate compound can inhibit the activity of a *P. aeruginosa* MurC polypeptide. According to this aspect a polynucleotide encoding the polypeptide is used to construct an expression vector appropriate for a particular host cell. The host cell is transformed or transfected with the expression vector and cultured under conditions conducive to the expression of the MurC polypeptide. The cell is contacted with the candidate. Finally, one measures the activity of the MurC polypeptide in the presence of the candidate. If the activity is lower relative to the activity of the protein in the absence of the candidate, then the candidate is a inhibitor of the MurC polypeptide. In preferred embodiments, the polynucleotide encodes a protein having an amino acid sequence of SEQ ID NO:2 or a naturally occurring mutant of polymorphic form thereof. In other preferred embodiments, the polynucleotide has the sequence of SEQ ID NO:1. In particular embodiments, the relative activity of MurC is determined by comparing the activity of the MurC in a host cell. In some embodiments, the host cell is disrupted and the candidate is contacted to the released cytosol. In other embodiments, the cells can be disrupted contacting with the candidate and before determining the activity of the MurC protein. Finally, according to this aspect the relative activity can determined by comparison to a previously measured or expected activity value for the MurC activity in the host under the conditions. However, in preferred embodiments, the relative activity is determined by measuring the activity of the Mur C in a control cell that was not contacted with a candidate compound. In particular embodiments, the host cell is a pseudomonad and the protein inhibited is the MurC produced by the pseudomonad.

An aspect of this invention is a compound that is an inhibitor of a *P. aeruginosa* MurC protein an assay described herein. In preferred embodiments, the compound is an inhibitor of a *P. aeruginosa* MurC protein produced by a host cell comprising an expression vector of this invention. In most preferred embodiments, the compound is also an inhibitor of MurC protein produced by a pathogenic strain *P. aeruginosa* and also inhibits the growth of said pseudomonad.

An aspect of this invention is a pharmaceutical preparation that includes an inhibitor of *P. aeruginosa* MurC and a pharmaceutically acceptable carrier.

An aspect of this invention is a method of treatment comprising administering a inhibitor of the *P. aeruginosa* MurC to a patient. The treatment can be prophylactic or therapeutic. In preferred embodiments, the appropriate dosage for a particular patient is determined by a physician.

By "about" it is meant within 10% to 20% greater or lesser than particularly stated.

As used herein an "inhibitor" is a compound that interacts with and inhibits or prevents a polypeptide of MurC from catalyzing the ATP-dependent addition of L-alanine to UDP-N-acetylmuramoyl precursor.

As used herein a "modulator" is a compound that interacts with an aspect of cellular biochemistry to effect an increase or decrease in the amount of a polypeptide of MurC present in, at the surface or in the periplasm of a cell, or in the surrounding serum or media. The change in amount of the MurC polypeptide can be mediated by the effect of a modulator on the expression of the protein, e.g., the transcription, translation, post-translational processing, translocation or folding of the protein, or by affecting a component(s) of cellular biochemistry that directly or indirectly participates in the expression of the protein. Alternatively, a modulator can act by accelerating or decelerating the turnover of the protein either by direct interaction with the protein or by interacting with another component(s) of cellular biochemistry which directly or indirectly effects the change.

All of the references cited herein are incorporated by reference in their entirety as background material.

BRIEF DESCRIPTION OF THE DRAWINGS

FIGS. 1A & 1B. Nucleotide sequence (SEQ ID NO: 1) and the predicted amino acid sequence (SEQ ID NO:2) of *P. aeruginosa* murC. The amino acid sequence (SEQ ID NO:2) is presented in three-letter code below the nucleotide sequence (nucleotides 59 to 1520 of SEQ ID NO: 1).

DETAILED DESCRIPTION OF THE INVENTION

This invention provides polynucleotides and polypeptides of a cell wall biosynthesis gene from *Pseudomonas aeruginosa*, referred to herein as MurC. The polynucleotides and polypeptides are used to further provide expression vectors, host cells comprising the vectors, probes and primers, antibodies against the MurC protein and polypeptides thereof, assays for the presence or expression of MurC and assays for the identification of modulators and inhibitors of MurC.

Bacterial MurC, UDP-N-acetylmuramyl:L-alanine ligase, a cytoplasmic peptidoglycan biosynthetic enzyme, catalyzes the ATP-dependent addition of L-alanine to the UDP-N-acetylmuramyl precursor, generating the UDP-N-acetylmuramoyl-L-alanine.

The murC gene was cloned from *Pseudomonas aeruginosa*. Sequence analysis of the *P. aeruginosa* murC gene revealed an open reading frame of 487 amino acids. The deduced amino acid sequence of *P. aeruginosa* MurC is homologous to MurC from *Escherichia coli, Haemophilus influenza, Bacillus subtilis* and *S. aureus*. Recombinant MurC protein from *P. aeruginosa* was over-produced as His-tagged fusion protein in *Escherichia coli* host cells and the enzyme was purified to apparent homogeneity. The recombinant enzyme catalyzed the ATP-dependent addition of L-alanine to the UDP-N-acetylmuramyl precursor.

Nucleic acids encoding murC from *Pseudomonas aeruginosa* are useful in the expression and production of the *P. aeruginosa* MurC protein. The nucleic acids are also useful in providing probes for detecting the presence of *P. aeruginosa*.

Polynucleotides

Polynucleotides useful in the present invention include those described herein and those that one of skill in the art will be able to derive therefrom following the teachings of this specification. A preferred aspect of the present invention is an isolated nucleic acid encoding a MurC protein of *Pseudomonas aeruginosa*. A preferred embodiment is a nucleic acid having the sequence disclosed in FIG. 1, SEQ ID NO:1 and disclosed as follows:

```
CTCCATGGCA GACCAGGCAC GCAGCCTGGC GAAACCCGAG GCTACCCGGA   (SEQ ID NO:1)

CGGTGGTCGA TGCCTGCCTG GAGGTGGCCC GTGGTTAAAG AACCGAATGG

CGTCACCCGG ACCATGCGCC GTATCCGCCG CATCCATTTC GTCGGCATCG

GCGGCGCCGG TATGTGCGGG ATCGCCGAAG TGCTGCTGAA CCTCGGCTAC

GAGGTATCCG GCTCGGACCT CAAGGCCTCG GCGGTGACCG AGCGCCTGGA

GAAGTTCGGC GCGCAGATCT TCATCGGCCA CCAGGCGGAA AACGCCGACG

GCGCCGACGT GCTGGTGGTG TCCAGTGCCA TCAACCGGGC CAACCCGGAA

GTGGCATCGG CCCTGGAACG GCGGATTCCG GTGGTGCCGC GTGCGGAGAT

GCTCGCCGAG CTGATGCGCT ACCGGCACGG CATCGCGGTA GCCGGCACCC

ACGGCAAGAC CACCACTACC AGCCTGATCG CCTCGGTGTT CGCCGCCGGC

GGCCTGGACC CGACCTTCGT CATCGGCGGC CGGCTGAACG CCGCCGGGAC

CAACGCCCAG CTCGGCGCCA GCCGCTACCT GGTGGCCGAG GCCGACGAGA

GCGACGCCAG CTTCCTGCAC CTGCAACCGA TGGTCGCGGT GGTCACCAAT

ATCGACGCCG ACCACATGGC GACCTACGGC GGCGACTTCA ACAAGCTGAA

GAAGACCTTC GTCGAGTTCC TCCACAACCT GCCGTTCTAC GGACTGGCGG

TGATGTGCGT GGATGATCCG GTTGTGCGTG AGATCCTCCC GCAGATCGCC

CGCCCGACCG TGACCTACGG CCTCAGCGAA GACGCCGACG TGCGCGCGAT

CAACATCCGC CAGGAAGGCA TGCGCACCTG GTTCACCGTG TTGCGCCCGG

AGCGCGAGCC GCTGGACGTC TCGGTGAACA TGCCCGGCCT GCACAACGTG

CTGAATTCCC TGGCGACCAT CGTCATCGCT ACCGACGAGG GCATCTCCGA

CGAAGCCATC GTCCAGGGGC TGTCCGGCTT CCAGGGCGTA GGCCGGCGCT

TCCAGGTCTA CGGCGAGCTG CAGGTCGAGG GTGGCAGCGT GATGCTGGTG

GACGATTACG GCCACCATCC GCGCGAAGTC GCCGCGGTGA TCAAGGCGAT

CCGTGGCGGT TGGCCGGAGC GTCGCCTGGT GATGGTCTAC CAGCCGCATC

GCTATACCCG TACCCGCGAC CTGTACGAAG ACTTCGTGCA GGTGCTGGGC

GAAGCCAACG TGCTGCTGTT GATGGAGGTC TATCCGGCCG GCGAAGAGCC

GATCCCGGGA GCCGACAGCC GCCAGCTGTG CCACAGCATC CGCCAGCGCG

GCCAGCTTGA CCCGATCTAC TTCGAGCGCG ACGCCGACCT GGCGCCGCTG

GTCAAGCCGC TGCTGCGCGC TGGCGACATC CTGCTTTGCC AGGGCGCTGG

CGATGTCGGC GGCCTGGCCC CGCAACTGAT CAAGAACCCG CTGTTCGCCG

GCAAGGGAGG GAAGGGCGCA TGAACCTTTG CCTCGATAGC CTGCTGAACG
```

The translation initiation and termination codons are underlined.

The isolated nucleic acid molecule of the present invention can include a ribonucleic or deoxyribonucleic acid molecule, which can be single (coding or noncoding strand) or double stranded, as well as synthetic nucleic acid, such as a synthesized, single stranded polynucleotide.

The present invention also relates to recombinant vectors and recombinant hosts, both prokaryotic and eukaryotic, which contain the substantially purified nucleic acid molecules disclosed throughout this specification.

As used herein a "polynucleotide" is a nucleic acid of more than one nucleotide. A polynucleotide can be made up of multiple polynucleotide units that are referred to by description of the unit. For example, a polynucleotide can comprise within its bounds a polynucleotide(s) having a coding sequence(s), a polynucleotide(s) that is a regulatory region(s) and/or other polynucleotide units commonly used in the art.

An "expression vector" is a polynucleotide having regulatory regions operably linked to a coding region such that, when in a host cell, the regulatory regions can direct the expression of the coding sequence. The use of expression vectors is well known in the art. Expression vectors can be used in a variety of host cells and, therefore, the regulatory regions are preferably chosen as appropriate for the particular host cell.

A "regulatory region" is a polynucleotide that can promote or enhance the initiation or termination of transcription or translation of a coding sequence. A regulatory region includes a sequence that is recognized by the RNA polymerase, ribosome, or associated transcription or translation initiation or termination factors of a host cell. Regulatory regions that direct the initiation of transcription or translation can direct constitutive or inducible expression of a coding sequence.

Polynucleotides of this invention contain full length or partial length sequences of the MurC gene sequences disclosed herein. Polynucleotides of this invention can be single or double stranded. If single stranded, the polynucleotides can be a coding, "sense," strand or a complementary, "antisense," strand. Antisense strands can be useful as modulators of the gene by interacting with RNA encoding the MurC protein. Antisense strands are preferably less than full length strands having sequences unique or specific for RNA encoding the protein.

The polynucleotides can include deoxyribonucleotides, ribonucleotides or mixtures of both. The polynucleotides can be produced by cells, in cell-free biochemical reactions or through chemical synthesis. Non-natural or modified nucleotides, including inosine, methyl-cytosine, deaza-guanosine, etc., can be present. Natural phosphodiester internucleotide linkages can be appropriate. However, polynucleotides can have non-natural linkages between the nucleotides. Non-natural linkages are well known in the art and include, without limitation, methylphosphonates, phosphorothioates, phosphorodithionates, phosphoroamidites and phosphate ester linkages. Dephospho-linkages are also known, as bridges between nucleotides. Examples of these include siloxane, carbonate, carboxymethyl ester, acetamidate, carbamate, and thioether bridges. "Plastic DNA," having, for example, N-vinyl, methacryloxyethyl, methacrylamide or ethyleneimine internucleotide linkages, can be used. "Peptide Nucleic Acid" (PNA) is also useful and resists degradation by nucleases. These linkages can be mixed in a polynucleotide.

As used herein, "purified" and "isolated" are utilized interchangeably to stand for the proposition that the polynucleotide, protein and polypeptide, or respective fragments thereof in question have been removed from the in vivo environment so that they exist in a form or purity not found in nature. Purified or isolated nucleic acid molecules can be manipulated by the skilled artisan, such as but not limited to sequencing, restriction digestion, site-directed mutagenesis, and subcloning into expression vectors for a nucleic acid fragment as well as obtaining the wholly or partially purified protein or protein fragment so as to afford the opportunity to generate polyclonal antibodies, monoclonal antibodies, or perform amino acid sequencing or peptide digestion. Therefore, the nucleic acids claimed herein can be present in whole cells or in cell lysates or in a partially or substantially purified form. It is preferred that the molecule be present at a concentration at least about five-fold to ten-fold higher than that found in nature. A polynucleotide is considered substantially pure if it is obtained purified from cellular components by standard methods at a concentration of at least about 100-fold higher than that found in nature. A polynucleotide is considered essentially pure if it is obtained at a concentration of at least about 1000-fold higher than that found in nature. We most prefer polynucleotides that have been purified to homogeneity, that is, at least 10,000–100,000 fold. A chemically synthesized nucleic acid sequence is considered to be substantially purified when purified from its chemical precursors by the standards stated above.

Included in the present invention are assays that employ further novel polynucleotides that hybridize to *P. aeruginosa* murf sequences under stringent conditions. By way of example, and not limitation, a procedure using conditions of high stringency is as follows: Prehybridization of filters containing DNA is carried out for 2 hr. to overnight at 65° C. in buffer composed of 6×SSC, 5× Denhardt's solution, and 100 µg/ml denatured salmon sperm DNA. Filters are hybridized for 12 to 48 hrs at 65° C. in prehybridization mixture containing 100 µg/ml denatured salmon sperm DNA and 5–20×10$^6$ cpm of $^{32}$P-labeled probe. Washing of filters is done at 37° C. for 1 hr in a solution containing 2×SSC, 0.1% SDS. This is followed by a wash in 0.1×SSC, 0.1% SDS at 50° C. for 45 min. before autoradiography.

Other procedures using conditions of high stringency would include either a hybridization step carried out in 5×SSC, 5× Denhardt's solution, 50% formamide at 42° C. for 12 to 48 hours or a washing step carried out in 0.2×SSPE, 0.2% SDS at 65° C. for 30 to 60 minutes.

Reagents mentioned in the foregoing procedures for carrying out high stringency hybridization are well known in the art. Details of the composition of these reagents can be found in, e.g., Sambrook, et al., 1989, Molecular Cloning: A Laboratory Manual, second edition, Cold Spring Harbor Laboratory Press. In addition to the foregoing, other conditions of high stringency which may be used are well known in the art.

Polypeptides

A preferred aspect of the present invention is a substantially purified form of the MurC protein from *Pseudomonas aeruginosa*. A preferred embodiment is a protein that has the amino acid sequence which is shown in FIG. 1, in SEQ ID NO:2 and disclosed as follows:

MetProAlaTrpArgTrpProValValLysGluProAsnGlyValThrArgThrMetArg    (SEQ ID NO:2)

ArgIleArgArgIleHisPheValGlyIleGlyGlyAlaGlyMetCysGlyIleAlaGlu

ValLeuLeuAsnLeuGlyTyrGluValSerGlySerAspLeuLysAlaSerAlaValThr

GluArgLeuGluLysPheGlyAlaGlnIlePheIleGlyHisGlnAlaGluAsnAlaAsp

GlyAlaAspValLeuValValSerSerAlaIleAsnArgAlaAsnProGluValAlaSer

AlaLeuGluArgArgIleProValValProArgAlaGluMetLeuAlaGluLeuMetArg

TyrArgHisGlyIleAlaValAlaGlyThrHisGlyLysThrThrThrThrSerLeuIle

AlaSerValPheAlaAlaGlyGlyLeuAspProThrPheValIleGlyGlyArgLeuAsn

AlaAlaGlyThrAsnAlaGlnLeuGlyAlaSerArgTyrLeuValAlaGluAlaAspGlu

SerAspAlaSerPheLeuHisLeuGlnProMetValAlaValValThrAsnIleAspAla

AspHisMetAlaThrTyrGlyGlyAspPheAsnLysLeuLysLysThrPheValGluPhe

LeuHisAsnLeuProPheTyrGlyLeuAlaValMetCysValAspAspProValValArg

GluIleLeuProGlnIleAlaArgProThrValThrTyrGlyLeuSerGluAspAlaAsp

ValArgAlaIleAsnIleArgGlnGluGlyMetArgThrTrpPheThrValLeuArgPro

GluArgGluProLeuAspValSerValAsnMetProGlyLeuHisAsnValLeuAsnSer

LeuAlaThrIleValIleAlaThrAspGluGlyIleSerAspGluAlaIleValGlnGly

LeuSerGlyPheGlnGlyValGlyArgArgPheGlnValTyrGlyGluLeuGlnValGlu

GlyGlySerValMetLeuValAspAspTyrGlyHisHisProArgGluValAlaAlaVal

IleLysAlaIleArgGlyGlyTrpProGluArgArgLeuValMetValTyrGlnProHis

ArgTyrThrArgThrArgAspLeuTyrGluAspPheValGlnValLeuGlyGluAlaAsn

ValLeuLeuLeuMetGluValTyrProAlaGlyGluGluProIleProGlyAlaAspSer

ArgGlnLeuCysHisSerIleArgGlnArgGlyGlnLeuAspProIleTyrPheGluArg

AspAlaAspLeuAlaProLeuValLysProLeuLeuArgAlaGlyAspIleLeuLeuCys

GlnGlyAlaGlyAspValGlyGlyLeuAlaProGlnLeuIleLysAsnProLeuPheAla

GlyLysGlyGlyLysGlyAla

The present invention also relates to biologically active fragments and mutant or polymorphic forms of MurC polypeptide sequence as set forth as SEQ ID NO: 2, including but not limited to amino acid substitutions, deletions, additions, amino terminal truncations and carboxy-terminal truncations such that these mutations provide for proteins or protein fragments of diagnostic, therapeutic or prophylactic use and would be useful for screening for modulators, and/or inhibitors of MurC function.

Using the disclosure of polynucleotide and polypeptide sequences provided herein to isolate polynucleotides encoding naturally occurring forms of MurC, one of skill in the art can determine whether such naturally occurring forms are mutant or polymorphic forms of MurC by sequence comparison. One can further determine whether the encoded protein, or fragments of any MurC protein, is biologically active by routine testing of the protein of fragment in a in vitro or in vivo assay for the biological activity of the MurC protein. For example, one can express N-terminal or C-terminal truncations, or internal additions or deletions, in host cells and test for their ability to catalyze the ATP-dependent addition of L-alanine to the UDP-N-acetylmuramyl precursor.

It is known that there is a substantial amount of redundancy in the various codons which code for specific amino acids. Therefore, this invention is also directed to those DNA sequences that encode RNA comprising alternative codons which code for the eventual translation of the identical amino acid.

Therefore, the present invention discloses codon redundancy which can result in different DNA molecules encoding an identical protein. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide. However, any given change can be examined for any effect on biological function by simply assaying for the ability to catalyze the ATP-dependent addition of L-alanine to an alanyl residue of the UDP-N-acetylmuramyl precursor as compared to an unaltered MurC protein.

It is known that DNA sequences coding for a peptide can be altered so as to code for a peptide having properties that are different than those of the naturally occurring peptide. Methods of altering the DNA sequences include but are not limited to site directed mutagenesis. Examples of altered properties include but are not limited to changes in the affinity of an enzyme for a substrate.

As used herein, a "biologically active equivalent" or "functional derivative" of a wild-type MurC possesses a biological activity that is substantially similar to the biological activity of a wild type MurC. The term "functional derivative" is intended to include the "fragments," "mutants," "variants," "degenerate variants," "analogs," "orthologues," and "homologues" and "chemical derivatives" of a wild type MurC protein that can catalyze the ATP-dependent addition of L-alanine to the UDP-N-acetylmuramyl precursor.

The term "fragment" refers to any polypeptide subset of wild-type MurC. The term "mutant" is meant to refer to a molecule that may be substantially similar to the wild-type form but possesses distinguishing biological characteristics. Such altered characteristics include but are in no way limited to altered substrate binding, altered substrate affinity and altered sensitivity to chemical compounds affecting biological activity of the MurC or MurC functional derivative. The term "variant" refers to a molecule substantially similar in structure and function to either the entire wild-type protein or to a fragment thereof. A molecule is "substantially similar" to a wild-type MurC-like protein if both molecules have substantially similar structures or if both molecules possess similar biological activity. Therefore, if the two molecules possess substantially similar activity, they are considered to be variants even if the exact structure of one of the molecules is not found in the other or even if the two amino acid sequences are not identical. The term "analog" refers to a molecule substantially similar in function to either the full-length MurC protein or to a biologically active fragment thereof.

As used herein in reference to a MurC gene or encoded protein, a "polymorphic" MurC is a MurC that is naturally found in the population of Pseudomonads at large. A polymorphic form of MurC can be encoded by a different nucleotide sequence from the particular murC gene disclosed herein as SEQ ID NO:1. However, because of silent mutations, a polymorphic murC gene can encode the same or different amino acid sequence as that disclosed herein. Further, some polymorphic forms MurC will exhibit biological characteristics that distinguish the form from wild-type MurC activity, in which case the polymorphic form is also a mutant.

A protein or fragment thereof is considered purified or isolated when it is obtained at least partially free from it's natural environment in a composition or purity not found in nature. It is preferred that the molecule be present at a concentration at least about five-fold to ten-fold higher than that found in nature. A protein or fragment thereof is considered substantially pure if it is obtained at a concentration of at least about 100-fold higher than that found in nature. A protein or fragment thereof is considered essentially pure if it is obtained at a concentration of at least about 1000-fold higher than that found in nature. We most prefer proteins that have been purified to homogeneity, that is, at least 10,000–100,000 fold.

Probes and Primers

Polynucleotide probes comprising full length or partial sequences of SEQ ID NO: 1 can be used to determine whether a cell or sample contains *P. aeruginosa* MurC DNA or RNA. The effect of modulators that effect the transcription of the murC gene can be studied via the use of these probes. A preferred probe is a single stranded antisense probe having at least the full length of the coding sequence of MurC. It is also preferred to use probes that have less than the full length sequence, and contain sequences specific for *P. aeruginosa* murC DNA or RNA. The identification of a sequence(s) for use as a specific probe is well known in the art and involves choosing a sequence(s) that is unique to the target sequence, or is specific thereto. It is preferred that polynucleotides that are probes have at least about 25 nucleotides, more preferably about 30 to 35 nucleotides. The longer probes are believed to be more specific for *P. aeruginosa* murC gene(s) and RNAs and can be used under more stringent hybridization conditions. Longer probes can be used but can be more difficult to prepare synthetically, or can result in lower yields from a synthesis. Examples of sequences that are useful as probes or primers for *P. aeruginosa* murC gene(s) are Primer A (sense)

5' TT<u>CATATG</u>CCTGCCTGGAGGTG 3'    (SEQ ID NO:3)

and Primer B (antisense)

5' TT<u>GGATCC</u>TCATGCGCCCTTCCCTCCCTTG 3' (SEQ ID NO:4).

These primers are nucleotides 55–76 (A) and the complement of nucleotides 1442–1464 (B) respectively, of SEQ ID NO:1. Restriction sites, underlined, for NdeI and BamHI are added to the 5' ends of the primers to allow cloning between the NdeI and BamHI sites of the expression vector pET-15b. However, one skilled in the art will recognize that these are only a few of the useful probe or primer sequences that can be derived from SEQ ID NO:1.

Polynucleotides having sequences that are unique or specific for *P. aeruginosa* murC can be used as primers in amplification reaction assays. These assays can be used in tissue typing as described herein. Additionally, amplification reactions employing primers derived from *P. aeruginosa* murC sequences can be used to obtain amplified *P. aeruginosa* murC DNA using the murC DNA of the cells as an initial template. The murC DNA so obtained can be a mutant or polymorphic form of *P. aeruginosa* murC that differs from SEQ ID NO:1 by one or more nucleotides of the MurC open reading frame or sequences flanking the ORF. The differences can be associated with a non-defective naturally occurring form or with a defective form of MurC. Thus, polynucleotides of this invention can be used in identification of various polymorphic *P. aeruginosa* murC genes or the detection of an organism having a *P. aeruginosa* murC gene. Many types of amplification reactions are known in the art and include, without limitation, Polymerase Chain Reaction, Reverse Transcriptase Polymerase Chain Reaction, Strand Displacement Amplification and Self-Sustained Sequence Reaction. Any of these or like reactions can be used with primers derived from SEQ ID NO:1.

Expression of MurC

A variety of expression vectors can be used to express recombinant MurC in host cells. Expression vectors are defined herein as nucleic acid sequences that include regulatory sequences for the transcription of cloned DNA and the translation of their mRNAs in an appropriate host. Such vectors can be used to express a bacterial gene in a variety of hosts such as bacteria, bluegreen algae, plant cells, insect cells and animal cells. Specifically designed vectors allow the shuttling of genes between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and regulatory sequences. A promoter is defined as a regulatory sequence that directs RNA polymerase to bind to DNA and initiate RNA synthesis. A strong promoter is one which causes mRNAs to be initiated at high frequency. Expression vectors can include, but are not limited to, cloning vectors, modified cloning vectors, specifically designed plasmids or viruses.

In particular, a variety of bacterial expression vectors can be used to express recombinant MurC in bacterial cells. Commercially available bacterial expression vectors which are suitable for recombinant MurC expression include, but are not limited to pQE (Qiagen), pET11a or pET15b (Novagen), lambda gt11 (Invitrogen), and pKK223-3 (Pharmacia).

Alternatively, one can express murC DNA in cell-free transcription-translation systems, or murC RNA in cell-free translation systems. Cell-free synthesis of MurC can be in batch or continuous formats known in the art.

One can also synthesize MurC chemically, although this method is not preferred.

A variety of host cells can be employed with expression vectors to synthesize MurC protein. These can include *E. coli*, *Bacillus*, and *Salmonella*. Insect and yeast cells can also be appropriate.

Following expression of MurC in a host cell, MurC polypeptides can be recovered. Several protein purification procedures are available and suitable for use. MurC protein and polypeptides can be purified from cell lysates and extracts, or from culture medium, by various combinations of, or individual application of methods including ultrafiltration, acid extraction, alcohol precipitation, salt fractionation, ionic exchange chromatography, phosphocellulose chromatography, lecithin chromatography, affinity (e.g., antibody or His-Ni) chromatography, size exclusion chromatography, hydroxylapatite adsorption chromatography and chromatography based on hydrophobic or hydrophillic interactions. In some instances, protein denaturation and refolding steps can be employed. High performance liquid chromatography (HPLC) and reversed phase HPLC can also be useful. Dialysis can be used to adjust the final buffer composition.

The MurC protein itself is useful in assays to identify compounds that modulate the activity of the protein—including compounds that inhibit the activity of the protein. The MurC protein is also useful for the generation of antibodies against the protein, structural studies of the protein, and structure/function relationships of the protein.

Modulators and Inhibitors of MurC

The present invention is also directed to methods for screening for compounds which modulate or inhibit a MurC protein. Compounds which modulate or inhibit MurC can be DNA, RNA, peptides, proteins, or non-proteinaceous organic or inorganic compounds or other types of molecules. Compounds that modulate the expression of DNA or RNA encoding MurC or are inhibitors of the biological function of MurC can be detected by a variety of assays. The assay can be a simple "yes/no" assay to determine whether there is a change in expression or function. The assay can be made quantitative by comparing the expression or function of a test sample with the levels of expression or function in a standard sample, that is, a control. A compound that is a modulator can be detected by measuring the amount of the MurC produced in the presence of the compound. An compound that is an inhibitor can be detected by measuring the specific activity of the MurC protein in the presence and absence of the compound.

The proteins, DNA molecules, RNA molecules and antibodies lend themselves to the formulation of kits suitable for the detection and anaysis of MurC. Such a kit would comprise a compartmentalized carrier suitable to hold in close confinement at least one container. The carrier would further comprise reagents such as recombinant MurC or anti-MurC antibodies suitable for detecting MurC. The carrier can also contain a means for detection such as labeled antigen or enzyme substrates or the like.

Pharmaceutical Compositions

Pharmaceutically useful compositions comprising a modulator or inhibitor of MurC can be formulated according to known methods such as by the admixture of a pharmaceutically acceptable carrier. Examples of such carriers and methods of formulation can be found in Remington's Pharmaceutical Sciences. To form a pharmaceutically acceptable composition suitable for effective administration, such compositions will contain an effective amount of the inhibitor.

Therapeutic, prophylactic or diagnostic compositions of the invention are administered to an individual in amounts sufficient to treat, prevent or diagnose disorders. The effective amount can vary according to a variety of factors such as the individual's condition, weight, sex and age. Other factors include the mode of administration. The appropriate amount can be determined by a skilled physician.

The pharmaceutical compositions can be provided to the individual by a variety of routes such as subcutaneous, topical, oral and intramuscular.

The term "chemical derivative" describes a molecule that contains additional chemical moieties which are not normally a part of the base molecule. Such moieties can improve the solubility, half-life, absorption, etc. of the base molecule. Alternatively the moieties can attenuate undesirable side effects of the base molecule or decrease the toxicity of the base molecule. Examples of such moieties are described in a variety of texts, such as Remington's Pharmaceutical Sciences.

Compounds identified according to the methods disclosed herein can be used alone at appropriate dosages. Alternatively, co-administration or sequential administration of other agents can be desirable.

The present invention also provides a means to obtain suitable topical, oral, systemic and parenteral pharmaceutical formulations for use in the methods of treatment of the present invention. The compositions containing compounds identified according to this invention as the active ingredient can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they can also be administered in intravenous (both bolus and infusion), intraperitoneal, subcutaneous, topical with or without occlusion, or intramuscular form, all using forms well known to those of ordinary skill in the pharmaceutical arts.

Advantageously, compounds of the present invention can be administered in a single daily dose, or the total daily dosage can be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal, hepatic and cardiovascular function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

The following examples are presented by the way of illustration and, because various other embodiments will be apparent to those in the art, the following is not to be construed as a limitation on the scope of the invention. For example, while particular preferred embodiments of the invention are presented herein, it is within the ability of persons of ordinary skill in the art to modify or substitute vectors, host cells, compositions, etc., or to modify or design protocols or assays, all of which may reach the same or equivalent performance or results as the embodiments shown herein.

EXAMPLE 1

General Materials and Methods

All reagents were purchased from SIGMA CHEMICAL CO., St. Louis, Mo., unless otherwise indicated. UDP-N-acetylmuramyl-L-alanine was synthesized and purified by a method known in the art (Jin, H., Emanuele, J. J., Jr., Fairman, R., Robertson, J. G., Hail, M. E., Ho, H.-T., Falk, P. and Villafranca, J. J, 1996. Structural studies of *Escherichia coli* UDP-N-acetylmuramate: L-alanine ligase, Biochemistry 35: 14423–14431).

DNA Manipulations Reagents and Techniques.

Restriction endonucleases and T4 ligase were obtained from GIBCO-BRL. Agarose gel electrophoresis and plasmid DNA preparations were performed according to published procedures (Sambrook, J., E. F. Fritsch, and T. Maniatis, 1989, Molecular cloning: a L, Laboratory Manual, 2nd ed. Cold Spring Harbor, NY: Cold Spring Harbor Laboratory). Recombinant plasmids containing *P. aeruginosa* murC were propagated in *E. coli* DH5a (GIBCO-BRL, Rockville, Md.) prior to protein expression in *E. coli* BL21(DE3)/plysS (NOVAGEN, Madison, Wis.). SDS-PAGE was performed with precast gels (NOVAGEN). DNA sequences were determined using an automated ABI PRISM™ DNA sequencer (PERKIN-ELMER ABI, Foster City, Calif.).

EXAMPLE 2

Cloning of *Pseudomonas aeruginosa* murC

Genomic DNA from *P. aeruginosa* (strain MB4439) was prepared from 100 ml late stationary phase culture in Brain Heart Infusion broth (DIFCO, Detroit, Mich.). Cells were washed with 0.2 M sodium acetate, suspended in 10 ml of TEG (100 mM Tris, pH 7, containing 10 mM EDTA and 25% glucose) and lysed by incubation with 200 µg of N-acetylmuramidase (SIGMA) for 1 h at 37° C. Chromosomal DNA was purified from the cell lysate using a QIAGEN (Santa Clarita, Calif.) genomic DNA preparation kit and following the manufacturers protocol. Briefly, the cell lysate was treated with protease K at 50° C. for 45 min, loaded onto an equilibrated QIAGEN genomic tip, entered into the resin by centrifugation at 3000 rpm for 2 min. Following washing the genomic tip, the genomic DNA was eluted in distilled water and kept at 4° C. Approximately 50 ng genomic DNA was used as a template in PCR reactions to clone murC.

Two oligonucleotide primers (GIBCO/BRL, Bethesda, Md.) complementary to sequences at the 5' and the 3' ends of *P. aeruginosa* murC were used to clone this gene using KLENTAQ ADVANTAGE™ polymerase (CLONTECH, Palo Alto, Calif.). The primer nucleotide sequences were as follows:

```
5'-TTCATATGCCTGCCTGGAGGTG-3'    (SEQ ID NO:3)
```

(a NdeI linker within nucleotides 55–76 of SEQ ID NO: 1) and

```
5'-TTGGATCCTCATGCGCCCTTCCCTCCCTTG-3'    (SEQ ID NO:4)
```

(a BamHI linker within the complement of nucleotides 1442–1464 of SEQ ID NO: 1). A PCR product representing *P. aeruginosa* murC was verified by nucleotide sequence, digested with NdeI and BamHI, and cloned between the NdeI and BamHI sites of pET-15b, creating plasmid pPaeMurC. This plasmid was used for expression of the murC gene in *E. coli*.

EXAMPLE 3

Sequence Analysis of *Pseudomonas aeruginosa* murC

The nucleotide sequence of murC, determined in both orientations, and the deduced amino acid sequence of the MurC protein is depicted in FIGS. 1A–1B. Sequence comparison using the BLAST algorithm (Altschul, S. F., Gish, W., Miller, W., Myers, E. W. & Lipman, D. J. (1990) "Basic local alignment search tool." J. Mol. Biol. 215:403–410) against the GenBank database showed that, to varying degrees, the cloned region is homologous (76% similar, 59% identical) to murC gene from *E. coli* (Ikeda, M., Wachi, M., Jung, H. K., Ishino, F. and Matsuhashi, M. 1990. Nucleotide sequence involving murG and murC in the mra gene cluster of *Escherichia coli*. Nucleic Acids Res. 18:4014).

EXAMPLE 4

Overexpression, Purification and Enzymatic Activity of *Pseudomonas aeruginosa* MurC murC was cloned into the expression vector pET-15b (NOVAGEN) as described above to create plasmid pPaeMurC. The pET-15b vector incorporates the 6× Histidine-tag into the protein construct to allow rapid purification of MurC by affinity chromatography. The pET (Plasmids for Expression by T7 RNA polymerase) plasmids are derived from pBR322 and designed for protein over-production in *E. coli*. The vector pET-15b contains the ampicillin resistance gene, ColE1 origin of replication in addition to T7 phage promoter and terminator. The T7 promoter is recognized by the phage T7 RNA polymerase but not by the *E. coli* RNA polymerase. A host *E. coli* strain such as BL21(DE3)pLysS is engineered to contain integrated copies of T7 RNA polymerase under the control of lacUV5 that is inducible by IPTG. Production of a recombinant protein in the *E. coli* strain BL21(DE3) pLysS occurs after expression of T7RNA polymerase is induced.

The pPaeMurC plasmid was introduced into the host strain BL21 DE3/pLysS (NOVAGEN) for expression of His-tagged MurC. Colonies were grown at 37° C. in 100 ml of LB broth containing 100 mg/ml ampicillin and 32 µg/ml chloramphenicol. When cultures reached a cell density of $A_{600}=0.5$, cells were pelleted and then resuspended in M9ZB medium (NOVAGEN) containing 1 mM IPTG. Cells were induced for 3 h at 30° C., pelleted at 3000 g, and frozen at −80° C.

Figure 2:
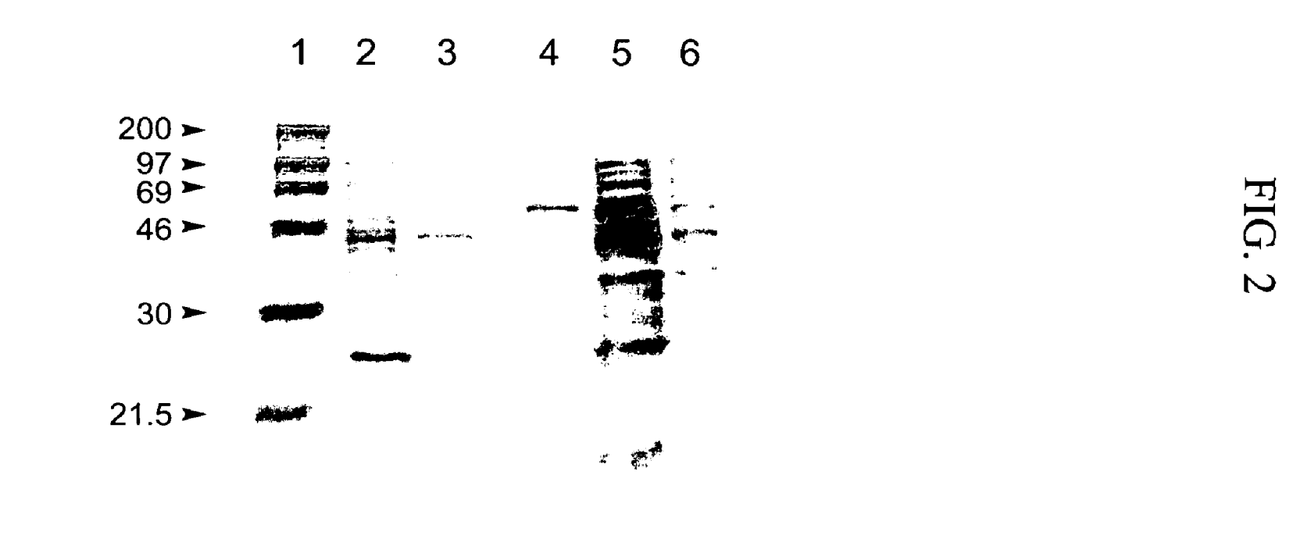
FIG. 2. Production of recombinant *P. aeruginosa* MurC. Lane 1, Molecular weight markers; Lane 2, IPTG-induced lysate of cells (BL21(DE3)/pLysS) containing the control vector pET-15b; Lane 3, uninduced cell lysate containing the control vector pET-15b; lane 4, column-purified MurC; Lane 5 IPTG-induced lysate of cells expressing MurC; Lane 6, uninduced lysate of cells containing murC.

Cultures containing either the recombinant plasmid pPaeMurC or the control plasmid vector, pET-15b were grown at 30° C. and induced with IPTG. Cells transformed with pPaeMurC contained an inducible protein of approximately 54.7 kDa, corresponding to the expected size of *P. aeruginosa* MurC protein as shown by SDS-PAGE. (FIG. 2.) There were no comparable detectable protein bands after induction of cells transformed with the control plasmid vector, pET-15b.

Purification of Recombinant MurC Enzyme

The cell pellet from 100 ml of induced culture prepared as described above was resuspended in 10 ml BT buffer (50 mM bis-tris-propane, pH 8.0, containing 100 mM potassium chloride and 1% glycerol) at 4° C. Cells were lysed either by freeze-thaw or by French Press. After centrifugation, the supernatant was mixed with 15 ml of freshly prepared TALON (CLONTECH) resin and incubated for 30 min at room temp. The resin was washed twice by centrifugation with 25 ml of BT buffer at room temperature. Finally, the resin was loaded into a column and washed with 20 ml of BT, pH 7.0, containing 5 mM imidazole. Protein was eluted with 20 ml of BT buffer pH 8.0, containing 100 mM imidazole. Fractions (0.5 ml) were collected and analyzed by SDS-Gel electrophoresis. (FIG. 2) This resulted in a partially purified preparation of *P. aeruginosa* MurC protein that could be used in activity assays. The protein may be purified further, if desired, using methods known in the art.

Assay for Activity of MurC Enzyme.

The ATP-dependent MurC activity was assayed by monitoring the formation of product ADP using the pyruvate kinase and lactate dehydrogenase coupled enzyme assay. The reaction was monitored spectrophotometrically.

Typically, the assay contained 100 mM BIS-TRIS-propane, pH 8.0, 200 μM NADH, 1 mM ATP, 20 mM PEP, 5 mM MgCl$_2$, 1 mM DTT, 350 μM UDP-N-acetyl-muramyl, 1 mM L-alanine, 33 units/ml of pyruvate kinase and 1660 units/ml of lactate dehydrogenase in a final volume of 200 or 400 μl. The mixture was incubated at 25° C. for 5 min and the reaction initiated by the addition of 1–10 μg of MurC. These conditions are one example of an assay useful for evaluating the activity of MurC. Other assays can be used, or amounts of buffers, substrate and enzyme can be changed, as desired, to alter the rate of production of ADP.

ADP formation was monitored by the decrease in absorbance at 340 nm as a function of time using a MOLECULAR DEVICES SPECTRAMAXPLUS™ microtiterplate spectrophotomer (for 200 μl assays) or a HEWLETT-PACKARD HP8452A spectrophotometer equipped with a circulating water bath (for 400 μl assays). Rates were calculated from the linear portions of the progress curves using the extinction coefficient for NADH, e=6220 cm$^{-1}$ M$^{-1}$. One unit of MurC activity is equal to 1 μmol of ADP formed per min at 25° C. MurC activity co-eluted with a ||51 kDa protein.

TABLE 1

Specific activities of recombinant MurC from *E. coli* and *P. aeruginosa*.

| Mur Ligase | *P. aeruginosa* μmol × min$^{-1}$ × mg$^{-1}$ | *E. coli* μmol × min$^{-1}$ × mg$^{-1}$ |
|---|---|---|
| MurC | 0.3 | 0.066 |

EXAMPLE 5

Screening for Inhibitors of MurC

One assay for the measurement of the activity of MurC is provided in Example 4. That assay, and other assays for MurC activity can be adapted for screening assays to detect inhibitors of MurC. For example, for inhibition assays, inhibitors in DMSO are added at the desired concentration to the assay mixture. In a separate, control reaction, only DMSO is added to the assay mixture. The reactions are initiated by the addition of enzyme (MurC). Rates are calculated as described above. Relative activities are calculated from the equation 1:

$$\text{relative activity} = \text{rate with inhibitor/rate without inhibitor.} \quad (1)$$

Inhibition constant (IC$_{50}$) values are determined from a range of inhibitor concentrations and calculated from equation 2.

$$\text{relative activity} = 1/(1+[I]/IC_{50}) \quad (2)$$

One can use computer software to assist in the analysis, e.g., SIGMA PLOT™ (JANDEL SCIENTIFIC, San Rafeal, Calif.).

We prefer inhibitors of MurC that result in relative activities of the MurC enzyme of at least less than 75%, more preferably, 25–50% or 10–25%. We most prefer inhibitors resulting in relative activities of less than 20%, particularly less than 10% of the activity of MurC in the absence of the inhibitor.

We also prefer inhibitors that effectively lower the relative activity of MurC when the inhibitor is present at a very low concentration.

EXAMPLE 8

Therapy Using Inhibitors of MurC

A patient presenting with an indication of infection with a microorganism susceptible to inhibitors of MurC, e.g., gram positive and negative bacteria, including *P. aeruginosa*, can be treated by administration of inhibitors of MurC. Physicians skilled in the art are familiar with administering therapeutically effective amounts of inhibitors or modulators of microbial enzymes. Such skilled persons can readily determine an appropriate dosing scheme to achieve a desired therapeutic effect.

Therapy can also be prophylactic. For example, a patient at risk for developing a bacterial infection, including infection with *P. aeruginosa*, can be treated by administration of inhibitors of MurC. Physicians skilled in the art are familiar with administering therapeutically effective amounts of inhibitors or modulators of microbial enzymes. Such skilled persons can readily determine an appropriate dosing scheme to achieve a desired therapeutic effect.

What is claimed is:

1. A purified and isolated polynucleotide encoding a polypeptide having the amino acid sequence of SEQ ID NO: 2.

2. The polynucleotide of claim 1 wherein the polynucleotide encoding the polypeptide of SEQ ID NO:2 is a DNA polynucleotide comprising the polynucleotide sequence of SEQ ID NO:1.

3. A purified and isolated polynucleotide that is an expression vector comprising the polynucleotide of claim 1.

4. A purified and isolated host cell comprising the expression vector of claim 3.

5. A process for expressing a MurC polypeptide of *Pseudomonas aeruginosa* in a recombinant host cell, comprising:
(a) transforming a suitable host cell with the expression vector of claim 3, and,
(b) culturing the host cell of step (a) in and under conditions which allow expression of said the MurC polypeptide from said expression vector.

6. A purified and isolated polypeptide having the amino acid sequence of SEQ ID NO: 2.

7. A method of determining whether a candidate compound is an inhibitor of a *Pseudomonas aeruginosa* MurC polypeptide comprising:
(a) providing at least one host cell harboring an expression vector that includes a polynucleotide encoding a polypeptide having the amino acid sequence of SEQ ID NO: 2, and
(b) culturing said host cell under conditions that promote the expression of said polypeptide, and
(c) contacting said at least one cell with the candidate to permit the interaction of the candidate with the MurC polypeptide, and
(d) determining whether the candidate is an inhibitor of the MurC polypeptide by ascertaining the activity of the polypeptide in the presence of the candidate.

8. The method of claim 7 wherein the polynucleotide encoding a polypeptide having the amino acid sequence of SEQ ID NO: 2 has the polynucleotide sequence of SEQ ID NO: 1.

9. The method of claim 7 wherein the determination of activity in step (d) comprises comparing a measurement of MurC polypeptide activity of said at least one cell before step (c) to a measurement of MurC polypeptide activity of said at least one cell after step (c).

10. A method of determining whether a candidate compound is an inhibitor of a *Pseudomonas aeruginosa* MurC polypeptide comprising:
(a) providing a sample that includes a MurC polypeptide having the amino acid sequence of SEQ ID NO: 2, and
(b) contacting said sample with the candidate to permit the interaction of the candidate with the MurC polypeptide, and
(c) determining whether the candidate is an inhibitor of the MurC polypeptide by ascertaining the activity of the MurC polypeptide in the presence of the candidate.

11. The method of claim 10 wherein in step (c) the activity is determined by comparing a measurement of MurC polypeptide activity of the sample before step (b) to a measurement of MurC polypeptide activity of the sample after step (b).

* * * * *